US00PP28676P3

(12) United States Plant Patent
Bernuetz

(10) Patent No.: US PP28,676 P3
(45) Date of Patent: Nov. 21, 2017

(54) ***EUPHORBIA* PLANT NAMED 'BONPRI 1095'**

(50) Latin Name: ***Euphorbia pulcherrima* Willd. ex Klotzsch×*Euphorbia cornastra***
Varietal Denomination: Bonpri 1095

(71) Applicant: Andrew Bernuetz, Silverdale (AU)

(72) Inventor: Andrew Bernuetz, Silverdale (AU)

(73) Assignee: Bonza Botanicals Pty., Ltd., Yellow Rock, NSW (AU)

( * ) Notice: Subject to any disclaimer, the term of this patent is extended or adjusted under 35 U.S.C. 154(b) by 9 days.

(21) Appl. No.: 14/999,203

(22) Filed: Apr. 11, 2016

(65) Prior Publication Data

US 2017/0295692 P1 Oct. 12, 2017

(51) Int. Cl.
*A01H 5/02* (2006.01)

(52) U.S. Cl.
USPC ..... Plt./302

(58) Field of Classification Search
USPC ..... Plt./302
See application file for complete search history.

*Primary Examiner* — Keith Robinson
(74) *Attorney, Agent, or Firm* — C. A. Whealy

(57) ABSTRACT

A new and distinct cultivar of *Euphorbia* plant named 'Bonpri 1095', characterized by its upright and mounded plant habit; vigorous growth habit; freely branching habit; dark green-colored leaves; inflorescences with large intense red purple-colored flower bracts with lighter red purple-colored margins; inflorescences with small and sterile cyathia; and good post-production longevity.

1 Drawing Sheet

Botanical designation: *Euphorbia pulcherrima* Willd. ex Klotzsch×*Euphorbia cornastra.*
Cultivar denomination: 'BONPRI 1095'.

BACKGROUND OF THE INVENTION

The present invention relates to a new and distinct cultivar of *Euphorbia* plant, an interspecific hybrid botanically known as *Euphorbia pulcherrima* Willd. ex Klotzsch×*Euphorbia cornastra*, and hereinafter referred to by the cultivar name 'Bonpri 1095'.

The new *Euphorbia* plant is a product of a planned breeding program conducted by the Inventor in Yellow Rock, New South Wales, Australia. The objective of the program is to create and develop new interspecific *Euphorbia* plants with upright and mounded plant habit and large attractive flower bracts.

The new *Euphorbia* plant originated from a cross-pollination by the Inventor on Nov. 1, 2010 of a proprietary selection of *Euphorbia pulcherrima* Willd. ex Klotzsch identified as code number 151, not patented, as the female, or seed, parent with a proprietary selection of *Euphorbia pulcherrima*×*Euphorbia cornastra* identified as code number 810, not patented, as the male, or pollen, parent. The new *Euphorbia* plant was discovered and selected by the Inventor as a single flowering plant within the progeny of the stated cross-pollination in a controlled greenhouse environment in Yellow Rock, New South Wales, Australia on Apr. 4, 2012.

Asexual reproduction of the new *Euphorbia* plant by terminal vegetative cuttings in a controlled greenhouse environment in Yellow Rock, New South Wales, Australia since April, 2012 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bonpri 1095'. These characteristics in combination distinguish 'Bonpri 1095' as a new and distinct *Euphorbia* plant:

1. Upright and mounded plant habit.
2. Vigorous growth habit.
3. Freely branching habit.
4. Dark green-colored leaves.
5. Inflorescences with large intense red purple-colored flower bracts with lighter red purple-colored margins.
6. Inflorescences with small and sterile cyathia.
7. Good post-production longevity.

In side-by-side comparisons, plants of the new *Euphorbia* differ primarily from plants of the female parent selection in the following characteristics:

1. Plants of the new *Euphorbia* have smaller flower bracts than plants of the female parent selection.
2. Plants of the new *Euphorbia* and the female parent selection differ in flower bract color as plants of the female parent selection have red-colored flower bracts.
3. Inflorescences of plants of the new *Euphorbia* have small and sterile cyathia whereas inflorescences of plants of the female parent selection have larger and fertile cyathia.

In side-by-side comparisons, plants of the new *Euphorbia* differ primarily from plants of the male parent selection in the following characteristics:

1. Plants of the new *Euphorbia* and the male parent selection differ in flower bract color as plants of the male parent selection have pale pink-colored flower bracts.

2. Inflorescences of plants of the new *Euphorbia* have smaller cyathia than inflorescences of plants of the male parent selection.
3. Inflorescences of plants of the new *Euphorbia* do not produce pollen whereas inflorescences of plants of the male parent selection produce pollen.

Plants of the new *Euphorbia* can be compared to plants of the *Euphorbia pulcherrima* Willd. ex Klotzsch×*Euphorbia cornastra* 'Bonpridepcom', disclosed in U.S. Plant Pat. No. 21,324. In side-by-side comparisons, plants of the new *Euphorbia* differ primarily from plants of 'Bonpridepcom' in the following characteristics:

1. Plants of the new *Euphorbia* are more vigorous than plants of 'Bonpridepcom'.
2. Plants of the new *Euphorbia* have smaller leaves than plants of 'Bonpridepcom'.
3. Plants of the new *Euphorbia* have more inflorescences per plant than plants of 'Bonpridepcom'.
4. Plants of the new *Euphorbia* have larger inflorescences with larger flower bracts than plants of 'Bonpridepcom'.
5. Inflorescences of plants of the new *Euphorbia* have smaller cyathia than inflorescences of plants of 'Bonpridepcom'.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the sheet is a side perspective view of a typical flowering plant of 'Bonpri 1095' grown in a container.

The photograph at the bottom of the sheet is a close-up view of typical inflorescences of 'Bonpri 1095'.

DETAILED BOTANICAL DESCRIPTION

Plants used in the aforementioned photographs and herewith described in detail were grown during the autumn in 12-cm containers in an outdoor nursery in Higashiomi, Shiga, Japan and under cultural practices typical of commercial *Euphorbia* production. During the production of the plants, day temperatures averaged 23° C. and night temperatures averaged 13° C. Plants were four months old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. ex Klotzsch×*Euphorbia cornastra* 'Bonpri 1095'.

Parentage:

*Female, or seed, parent*.—Proprietary selection of *Euphorbia pulcherrima* Willd. ex Klotzsch identified as code number 151, not patented.

*Male, or pollen, parent*.—Proprietary selection of *Euphorbia pulcherrima*×*Euphorbia cornastra* identified as code number 810, not patented.

Propagation:

*Type*.—Terminal vegetative cuttings.

*Time to initiate roots, summer*.—About ten days at temperatures about 18° C. to 25° C.

*Time to initiate roots, winter*.—About twelve days at temperatures about 16° C. to 20° C.

*Time to produce a rooted young plant, summer*.—About three weeks at temperatures about 18° C. to 25° C.

*Time to produce a rooted young plant, winter*.—About four weeks at temperatures about 16° C. to 20° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant habit and form*.—Upright and mounded plant habit; inverted triangle; inflorescences positioned above the foliar plane; vigorous growth habit.

*Plant height*.—About 32 cm.

*Plant diameter or spread*.—About 40 cm.

*Lateral branch description*.—Branching habit: Freely branching habit, about nine lateral branches develop per plant. Length: About 21 cm. Diameter: About 5.7 mm. Internode length: About 2.6 cm. Aspect: Mostly upright to somewhat outwardly. Strength: Strong. Texture: Smooth, glabrous. Color: Close to 144A.

*Leaf description*.—Arrangement: Alternate, simple. Length: About 6.6 cm. Width: About 4.1 cm. Shape: Deltoid or ovate. Apex: Acute. Base: Rounded or truncate. Margin: Shallowly serrate; undulate. Texture, upper and lower surfaces: Pubescent; rough. Venation pattern: Pinnate, reticulate. Color: Developing leaves, upper surface: Close to 141B. Developing leaves, lower surface: Close to 138B. Fully developed leaves, upper surface: Close to 139A; venation, close to 138C. Fully developed leaves, lower surface: Close to 138A; venation, close to 138D. Petioles: Length: About 2.1 cm. Diameter: About 1.5 mm. Texture, upper and lower surfaces: Pubescent. Color, upper surface: Close to 144A tinged with close to 177A. Color, lower surface: Close to 144A.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—About nine inflorescences develop per plant.

*Inflorescence diameter*.—About 20.9 cm.

*Inflorescence height*.—About 6.5 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering habit, plants flower about 50 days under natural season conditions in Japan.

*Post-production longevity*.—Good post-production longevity; plants of the new *Euphorbia* maintain good substance and bract color for about seven weeks.

*Flower bracts*.—Quantity per inflorescence: About seven. Length, largest bracts: About 9.8 cm. Width, largest bracts: About 5.4 cm. Shape: Ovate. Apex: Acuminate. Base: Rounded. Margin: Entire with shallow lobes. Texture and luster, upper surface: Smooth, glabrous; matte. Texture and luster, lower surface: Pubescent; matte. Aspect: Mostly horizontal. Venation pattern: Pinnate, reticulate. Color: Transitional bracts, upper surface: Close to N137A and 58C. Transitional bracts, lower surface: Close to 138B and 36D. Developing bracts, upper surface: Close to darker than 53C. Developing bracts, lower surface: Close to 53D. Fully expanded bracts, upper surface: Close to N57A; towards the margins, close to N57D; venation, close to N137A. Fully expanded bracts, lower surface: Close to 58D; venation, close to 145C. Flower bract petioles: Length: About 1.6 cm. Diameter: About 1.4 mm. Texture, upper and lower surfaces: Pubescent. Color, upper and lower surfaces: Close to 144C.

*Cyathia*.—Quantity per corymb: About 18, relatively small. Diameter of cyathia cluster: About 2.4 cm. Height, individual cyathium: About 2.6 mm. Diameter, individual cyathium: About 2.2 mm. Shape, individual cyathium: Globose; sessile. Color: Close to 144C; towards the apex, close to 60A. Nectaries: Plants of the new *Euphorbia* have not been observed to develop nectaries.

*Peduncles*.—Length: About 3.2 mm. Diameter: About 1.4 mm. Strength: Strong. Aspect: Upright to outwardly. Texture: Smooth, glabrous. Color: Close to 143B.

*Reproductive organs*.—Stamens: Plants of the new *Euphorbia* have not been observed to develop stamens. Pistils: Plants of the new *Euphorbia* have not been observed to develop pistils. Seeds and fruits: Seed and fruit production has not been observed on plants of the new *Euphorbia*.

Disease & pest resistance: Plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'Bonpri 1095' as illustrated and described.

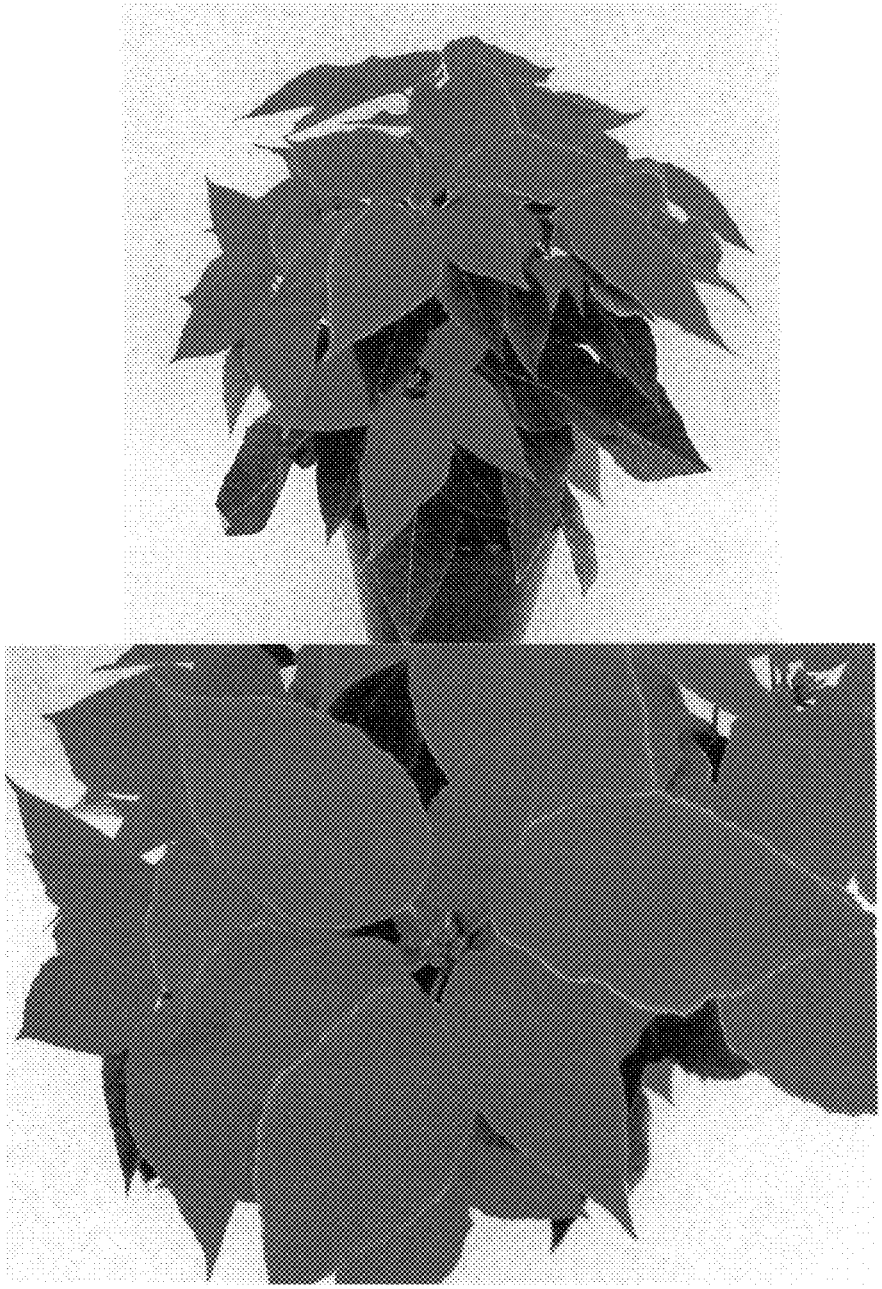

* * * * *